United States Patent [19]

Richey et al.

[11] 4,143,273

[45] Mar. 6, 1979

[54] VARIABLE COLLIMATOR

[75] Inventors: Joseph B. Richey, Shaker Heights; Thomas R. McBride, Chardon; John Covic, Wickliffe, all of Ohio

[73] Assignee: Ohio-Nuclear, Inc., Solon, Ohio

[21] Appl. No.: 786,358

[22] Filed: Apr. 11, 1977

[51] Int. Cl.² ............................................. A61B 6/02
[52] U.S. Cl. ............................ 250/445 T; 250/512; 250/514
[58] Field of Search ........... 250/513, 512, 511, 445 T, 250/401, 514

[56] References Cited

U.S. PATENT DOCUMENTS

| | | | |
|---|---|---|---|
| 2,331,586 | 10/1943 | Waisco | 250/511 |
| 2,911,537 | 11/1959 | Land | 250/513 |
| 3,502,878 | 3/1970 | Stewart et al. | 250/512 |
| 4,051,377 | 9/1977 | Kemner et al. | 250/401 |
| 4,066,901 | 1/1978 | Seppi et al. | 250/511 |

*Primary Examiner*—Alfred E. Smith
*Assistant Examiner*—T. N. Grigsby
*Attorney, Agent, or Firm*—Fay & Sharpe

[57] ABSTRACT

An automatic variable collimator which controls the width and thickness of X-ray beams in X-ray diagnostic medical equipment, and which is particularly adapted for use with computerized axial tomographic scanners. A two-part collimator is provided which shapes an X-ray beam both prior to its entering an object subject to radiographic analysis and after the attenuated beam has passed through the object. Interposed between a source of radiation and the object subject to radiographic analysis is a first or source collimator. The source collimator causes the X-ray beam emitted by the source of radiation to be split into a plurality of generally rectangular shaped beams. Disposed within the source collimator is a movable aperture plate which may be used to selectively vary the thickness of the plurality of generally rectangular shaped beams transmitted through the source collimator. A second or receiver collimator is interposed between the object subject to radiographic analysis and a series of radiation detectors. The receiver collimator is disposed to receive the attenuated X-ray beams passing through the object subject to radiographic analysis. Located within the receiver collimator are a plurality of movable aperture plates adapted to be displaced relative to a plurality of fixed aperture plates for the purpose of varying the width and thickness of the attenuated X-ray beams transmitted through the object subject to radiographic analysis. The movable aperture plates of the source and receiver collimators are automatically controlled by circuitry which is provided to allow remote operation of the movable aperture plates.

26 Claims, 17 Drawing Figures

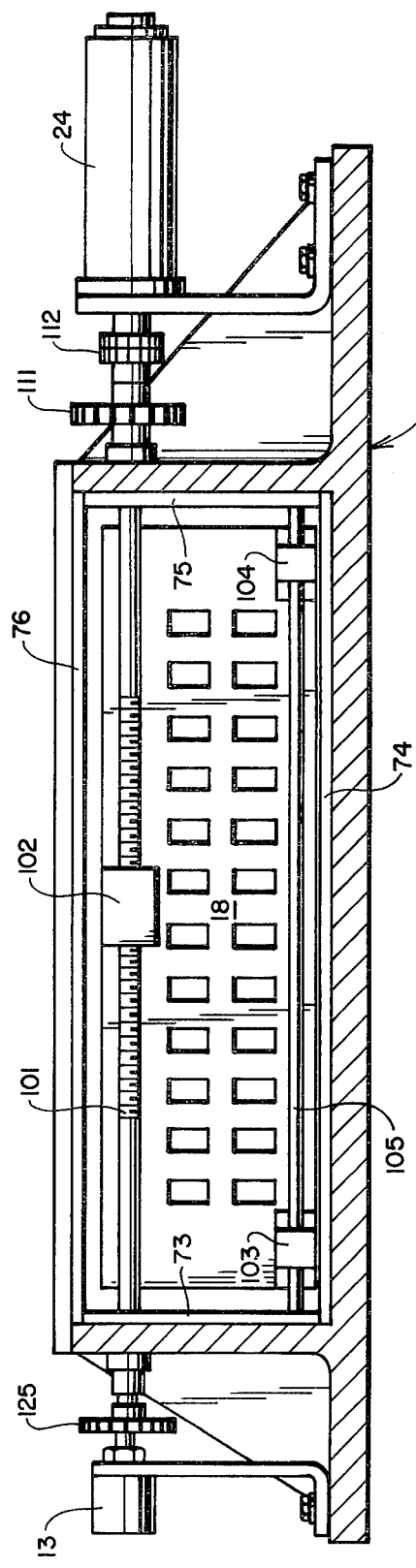
FIG. 9
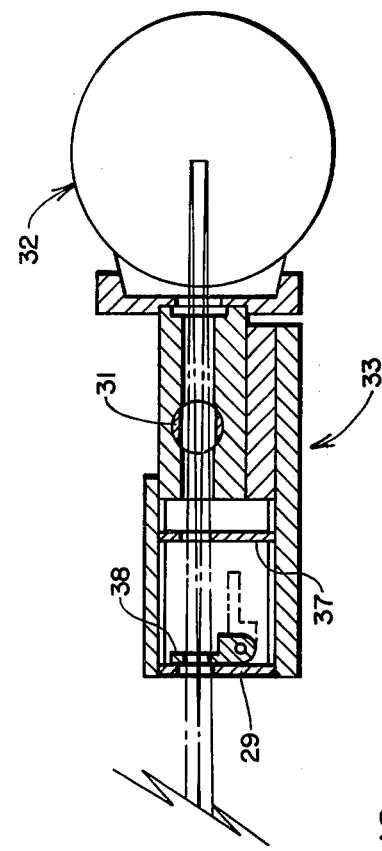
FIG. 10
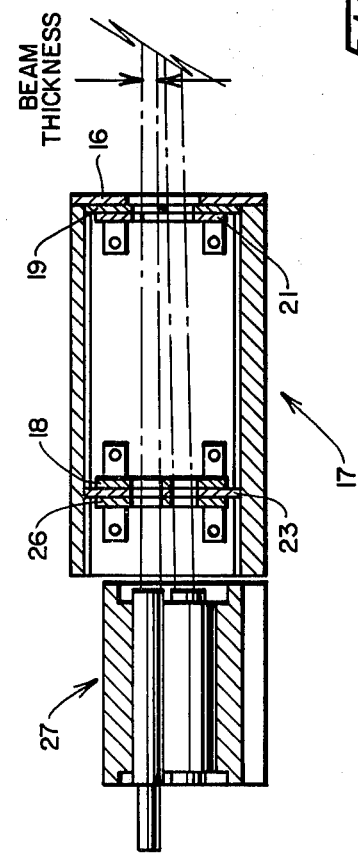

VARIABLE COLLIMATOR

BACKGROUND OF THE INVENTION

1. Field of the Invention

The present invention relates generally to X-ray apparatus and more particularly to a collimator structure therefor. Specifically, the invention is concerned with an apparatus which automatically controls the width and thickness of X-ray beams in X-ray diagnostic equipment, and is particularly adapted for use with a device known as a computerized axial tomographic scanner.

2. Description of the Prior Art

Collimators for controlling the size and shape of X-ray beams are well known in the art and include those shown in Haupt U.S. Pat. No. 2,542,196, Akaski et al U.S. Pat. No. 2,851,610 and Hura U.S. Pat. No. 3,829,701.

Mechanisms known as collimators are commonly used to shape an X-ray beam to a desired size and shape. In equipment used in radiographic studies, these collimators generally include two pairs of relatively movable diaphragms which shape an X-ray beam so as to provide a rectangular cross-section. These diaphragms are also used to eliminate two sources of extraneous radiation which may cause a degradation of the image produced by the diagnostic equipment.

A first cause of extraneous radiation is commonly referred to as scatter. In radiographic studies, it is desirable to confine the X-ray beam to the area of the object under examination, not only to minimize the exposure of the object and attending persons to the primary beam, but also to minimize radiation scatter effects. Radiation scatter is produced when the primary radiation beam strikes an object and is defracted. If the size of the X-ray beam is larger than required to accommodate a particular area under investigation, the X-ray beam striking areas of the object around the area of investigation will produce an unnecessary amount of radiation scatter which has the effect of reducing the contrast of the radiographic image.

A second source of extraneous radiation which may cause image degradation is caused by what is known as the "penumbra" effect. The X-ray beams are emitted from a very small area on an X-ray tube anode known as the focal point. Theoretically, this spot can be so small and bombardment of it with electrons so precise that the beam is emitted in a precise and regular conical pattern of "on focus" radiation. As a practical matter, however, the spot is a larger area than a theoretically optimized spot and an X-ray tube emits a penumbra or band of so-called "off focus" radiation from areas around the spot. This penumbra or "off focus" radiation is another source of image degradation.

Computerized axial tomographic X-ray scanners which provide the reconstruction of a transaxial section of an object by means of X-rays are also well known in the art as evidenced by Hounsfield U.S. Pat. No. 3,778,614. A reconstructed image of an object can be obtained by viewing an object via X-ray imaging from numerous angles, mathematically reconstructing the detailed structure, and displaying the reconstructed image. In general, X-ray beams are passed through the object for detection by scintillation crystal detectors. Analog outputs from these detectors go through signal conditioning circuitry that amplifies, clips and shapes the signals. A relatively simple analog to digital converter then prepares the signals for the computer, which performs various mathematical operations upon the data received and provides an output which may be used to display the reconstructed image.

Prior art computerized axial tomographic scanners have generally utilized fixed type collimators as evidenced by Hounsfield U.S. Pat. No. 3,778,614, the disclosure of which is incorporated by reference. In the case of a computerized axial tomographic scanner having a plurality of radiation detectors, the conventionally used collimator structure requires a rather complex apparatus which is expensive to fabricate and greatly increases the bulk of that portion of the scanner which is required to be moved, with the attendant disadvantages.

Even further, the conventional collimator structure is difficult to use because of its inflexibility. This inflexibility becomes readily apparent when it is desired to use a different size or shape X-ray beam during the scanning process. In order to realize this feature with the conventional collimator structure, it is necessary to entirely remove the collimator structure and replace it with a collimator structure producing the desired size or shape of X-ray beam. The expense and inconvenience of such a procedure often makes it unfeasible to effect a change in the size or shape of the X-ray beam used by the scanner.

There is, therefore, a need for a computerized axial tomographic scanner having a variable collimator means which may be used to readily change the size or shape of the X-ray beam utilized by the scanner, which change may be accomplished with relative ease and in a short period of time, and which provides a collimator means that minimizes extraneous radiation in order to enhance image quality.

The present invention solves this problem by providing an automatic variable collimator structure which utilizes a two-part collimator structure having movable aperture plates therein to effectively change the size and shape of the X-ray beams utilized by the scanner. The collimator structure additionally minimizes extraneous radiation.

SUMMARY OF THE INVENTION

This invention relates to an automatic variable collimator which controls the shape of X-ray beams in radiographic equipment. A two-part collimator structure, which is comprised of a first or source collimator and a second or receiver collimator, is utilized to shape X-ray beams both prior to their entering the object subject to radiographic analysis and after the attenuated beams have passed through the object. Interposed between a source of radiation and the object subject to radiographic analysis is the first or source collimator which causes the X-ray beams emitted by the source of radiation to be split into a plurality of generally rectangular shaped beams. Within the source collimator is disposed a movable aperture plate which may be used to selectively vary the thickness of the plurality of generally rectangular shaped beams transmitted through the source collimator. The movable aperture plate is displaced by a motor means actuated by a control circuitry. A second or receiver collimator is interposed between the object subject to radiographic analysis and a series of radiation detectors. The receiver collimator is disposed to receive the attenuated X-ray beams passing through the object subject to radiographic analysis. Within the receiver collimator are a plurality of movable aperture plates which may be displaced by motor means relative to a plurality of fixed aperture plates for the purpose of varying the width and thickness of the attenuated X-ray beams received from the object subject to radiographic analysis. A first and second receiver collimator motor means may be actuated by the control circuitry to provide a movement of the movable aperture plates in order to cause the X-ray beams passing therethrough to change their shape.

BRIEF DESCRIPTION OF THE DRAWINGS

FIG. 9 is a front sectional view of the receiver collimator shown in FIG. 8 and taken along line 9—9;

FIG. 10 is a partial left sectional view of the transport frame and collimator structure shown in FIG. 1 and taken along the line 10—10;

DETAILED DESCRIPTION OF THE DRAWINGS

Figure 1:
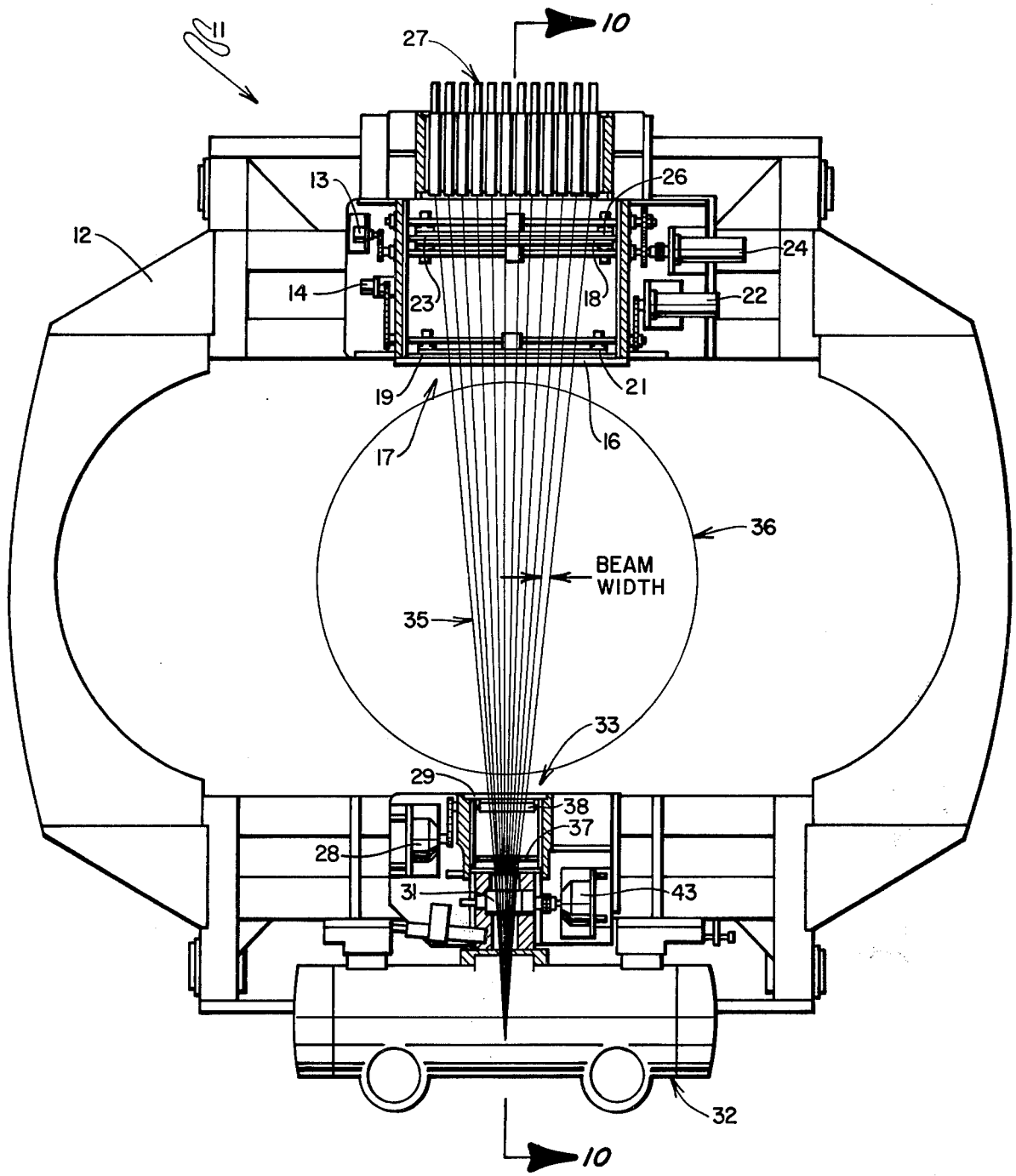
FIG. 1 is a side elevation of a transport frame used in a computerized tomographic scanner having the collimator structure mounted thereon, which collimator structure is shown in section to more fully illustrate the details of construction thereof.

Shown in FIG. 1 is a computerized axial tomographic scanner transport member 11 which is comprised of a movable frame member 12 which has fixedly attached thereto a source of radiation 32, a source collimator 33, a receiver collimator 17, and a series of receiver detectors denoted by the reference numeral 27. The source of radiation 32, the source collimator 33, the receiver collimator 17, and the receiver detectors are all in substantial axial alignment so that a beam of radiation emitted by the source of radiation 32 will be directed through the source collimator 33 to the receiver collimator 17 and finally received by the receiver detectors 27. The path of radiation from the source of radiation 32 to the receiver detectors 27 is indicated by the lines designated 35 which represent X-ray beam paths. The beam width, as referred to herein, is as indicated in FIG. 1 and is normally measured on the center line of the scan circle 36.

It may now be appreciated that by selective transverse and rotational movement of the transport member 11, the outputs of the receiver detectors 27 are able to provide an output which may be used by data processing means in the reconstruction of an image representation of an object contained within the scan circle 36.

The source of radiation 32 emits X-rays in a general cone-shaped configuration with the apex of the cone located at the focal spot of an X-ray tube contained within the source of radiation 32, as indicated by the X-ray beams 35. The cone angle is initially shaped by the opening in the source of radiation housing and secondarily by the safety shutter mechanism 31 contained within the source collimator 33.

Further shaping of the X-ray beams is effected by aperture plates 29 and 37 in order to provide for the transmission through the source collimator 33 a series of 12 rectangular beams. Further shaping of the X-ray beams may be optionally performed by the rotatable aperture plate 38, which may be rotationally disposed within the beam path 35 in order to effect a shaping thereof so as to reduce the thickness of the series of rectangular beams transmitted through the source collimator 33.

Figure 3:
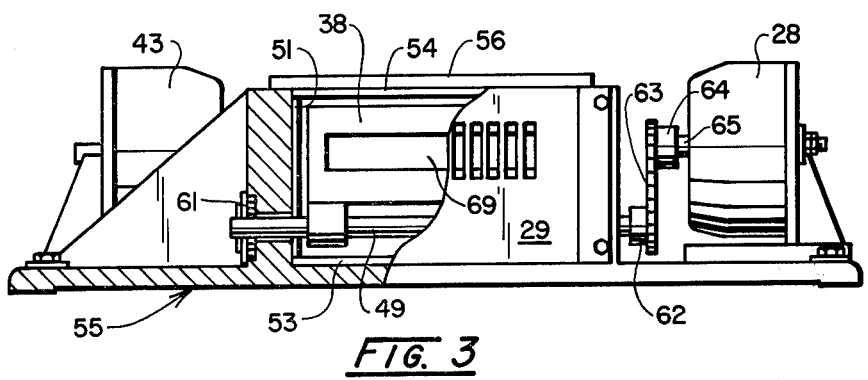
FIG. 3 is a front view of the source collimator having portions thereof broken away and shown in section.

Aperture means includes those structures which define an aperture. For example, plate 29 and, in the position of FIG. 3, plate 38 surround and define each beam shaping aperture.

There is thus provided a means for subjecting an object within the scan circle 36 to a series of 12 rectangular beams of radiation, which beams may be optionally 1 of 2 thicknesses.

The X-ray beams transmitted through the source collimator 33 are modulated and attenuated by objects within the scan circle 36 and transmitted to the receiver collimator 17 which causes further shaping of the X-ray beams and subsequently causes the X-ray beams to impinge upon receiver detectors 27. The output of the receiver detectors 27 may be processed to provide an image reconstruction of the objects located within the scan circle 36.

The receiver detectors 27 are preferably high atomic weight scintillators, such as those containing efficient radiation detectors like sodium iodide, or calcium fluoride. Photomultipliers may then be used as noiseless gain stages to convert the scintillation light into a direct current which may be subsequently used in the reconstruction of the image as is conventionally done in computerized axial tomographic scanners.

Figure 2:
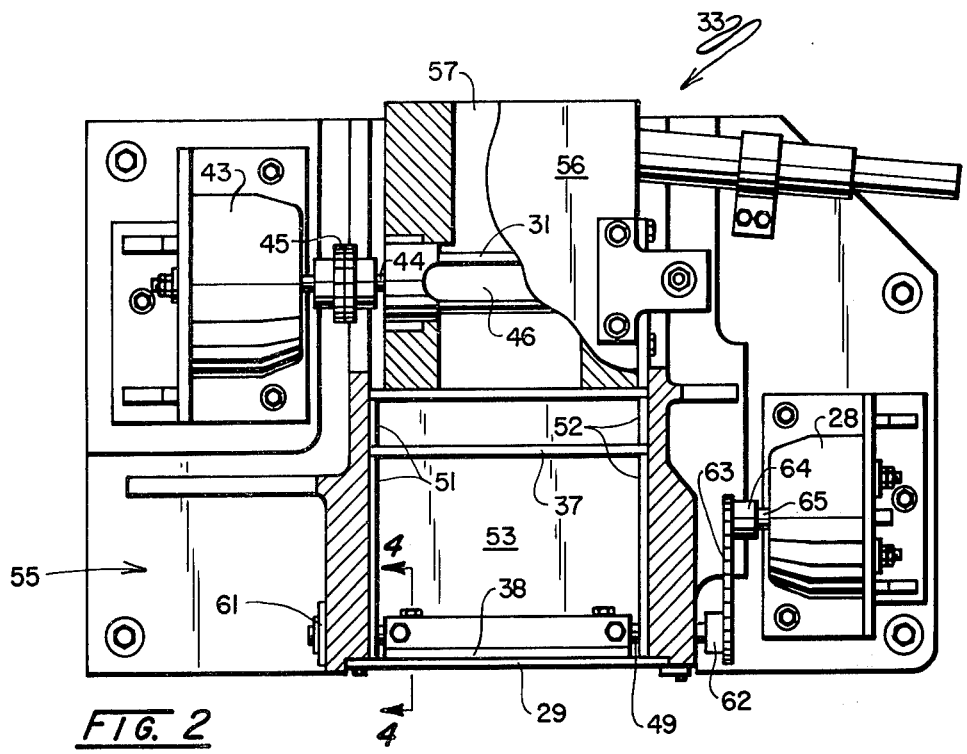
FIG. 2 is a top plan view of the source collimator having parts thereof broken away and shown in section in order to more fully illustrate details of construction thereof.

Referring now to FIG. 2 of the drawings, there is disclosed the source collimator 33 with parts broken away and shown in section to more fully illustrate the details of construction thereof. The source collimator 33 is generally comprised of a housing member 55 which, in the exemplary embodiment, is an aluminum casting. The housing member 55 in cooperation with cover plate 56 defines an X-ray collimator space within which are located the various beam shaping members. Disposed within this space formed by the housing member 55 and the cover plate 56 are interlocking lead plates, designated 51 through 54, which are used to confine the travel of X-ray beams through the source collimator 33 to a predetermined path.

X-ray beams are emitted from the source of radiation 32 into the collimator space through collimator space opening 57. A safety shutter 31 having an aperture 46 therein is provided to control the emission of X-ray beams into the remainder of the collimator space. As shown in FIG. 2, the safety shutter 31 is in its closed position wherein X-ray beams entering the collimator space opening 57 are not allowed to be transmitted to the remainder of the collimator space. When it is desired to introduce X-ray beams into the remainder of the collimator space, the safety shutter 31 may be rotated about its longitudinal axis by an electrically actuated rotary solenoid 43 which is mechanically coupled to the shaft 44 of the safety shutter 31 by means of a chain coupling 45.

It may now be readily seen that the rotary solenoid 43 may be electrically actuated to impart a rotary displacement to the safety shutter 31 via chain coupling 45 and safety shutter shaft 44 to thereby cause the safety shutter aperture 46 to be disposed within the collimator space so as to allow passage of X-ray beams therethrough. The X-ray beam passing through the safety shutter aperture 46 assumes the general size and shape of the aperture opening in the shutter.

Figure 7:
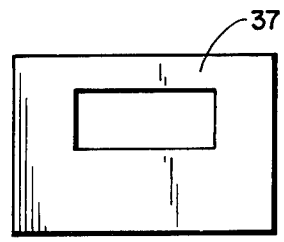
FIG. 7 is a front elevation of the fixed aperture plate of the source collimator.

X-ray beams passing through the aperture in the safety shutter 31 impinge upon a first fixed aperture plate 37 which has an opening therein of the general size and shape of the aperture 46 in the safety shutter. The purpose of the first fixed aperture plate 37, disclosed more fully in FIG. 7, is to effect the first stage of X-ray beam shaping or collimation. In addition, the fixed aperture plate 37 serves as a baffle to reduce the release of scatter X-rays or secondary emission into the patient compartment.

Figure 6:
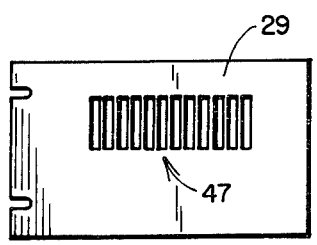
FIG. 6 is a front elevation of the second fixed aperture plate of the source collimator.

At the exit end of the collimator housing 55 is a second fixed aperture plate 29. The second fixed aperture plate 29, as more fully illustrated in FIG. 6, is preferably made of a tungsten alloy and has a series of 12 rectangular openings 47 through it. The second fixed source plate 29 effects a second stage of beam shaping by separating the X-ray beam into 12 smaller rectangularly shaped beams. In order to reduce the emission of scattered and unusable X-rays into the patient compartment, the second aperture plate 29 is placed as near to the periphery of the scan circle 36 and as far from the first fixed aperture plate 37 as practical.

The beams of X-rays, as collimated at this point, are approximately 13 millimeters thick at the center line of the scanned circle.

Figure 4:
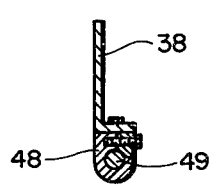
FIG. 4 is a partial sectional view of the source collimator shown in FIG. 2 and taken along the lines 4—4 showing the details of construction of the movable aperture plate.
Figure 5:
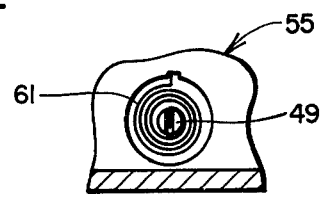
FIG. 5 is a partial left side view with parts removed of the source collimator shown in FIG. 3 disclosing the details of construction of the return spring.

In addition to the two fixed aperture plates 37 and 29, the source collimator 33 contains a movable aperture plate 38 interposed between the first fixed aperture plate 37 and the second fixed aperture plate 29 and adjacent to the second fixed aperture plate 29. The movable aperture plate 38, as more clearly disclosed in FIG. 4, is fixedly attached to a mounting bracket 48 which is in turn fixedly attached to movable aperture plate shaft 49 and rotates therewith. The rotating shaft 49 extends through the collimator housing 55 and has affixed to one end thereof a return spring 61. The return spring 61, as more fully shown in FIG. 5, has one end thereof fixedly attached to the rotating shaft 49 and the other end thereof fixedly attached to the housing member 55 in order to spring bias the rotating shaft 49.

The other end of the rotating shaft 49 has fixedly attached thereto a sprocket 62. The sprocket 62 is engaged with chain 63 which is in further engagement with sprocket 64 which is fixedly attached to the shaft 65 of the rotary solenoid 28. It may now be appreciated that electrical actuation of the rotary solenoid 28 will cause the shaft 65, the sprocket 64, chain 63, sprocket 62, and consequently shaft 49 to rotate in response thereto and that upon removal of the electrical actuation of the rotary solenoid 28, the rotating shaft 49 will tend to assume a "normal" position due to the spring biasing afforded by return spring 61.

This arrangement permits the rotatable plate 38 to be rotated 90 degrees into a masking position adjacent to the second fixed plate 29 whereby the opening of the movable aperture plate 38, which is smaller than the rectangular openings of the second fixed aperture plate 29, will mask the upper and lower portions of the twelve openings in the second fixed aperture plate 29, thereby effectively reducing the aperture height to produce a series of beams which are approximately 8 millimeters thick at the center line of the scan circle. There is thus provided a means for reducing the thickness of the X-ray beams transmitted through the source collimator 33. Beam thickness, as used herein, is defined in FIG. 10 of the drawings with the thickness normally being measured at the center line of the scan circle.

In the exemplary embodiment, when the operator elects to reduce the X-ray beam slice thickness from 13 millimeters to 8 millimeters, a select switch is indexed which causes the energization of the rotary solenoid 28 which is mounted on the collimator housing 55. The rotary action of the solenoid 28 moves the movable aperture plate 38 into a masking position adjacent to the fixed aperture plate 29.

When the operator elects to change beam thickness from 8 millimeters to 13 millimeters, the select switch is changed to de-energize the solenoid 28 and permit the spring 61 to return the movable aperture plate 38 to its non-masking position. This position is shown more clearly in FIG. 10 where the movable aperture plate 38 is shown in solid lines in the masking position, and is shown by phantom lines in its non-masking position. The control circuitry for causing the selective energization of the rotary solenoid 28 is described below in more detail.

Figure 8:
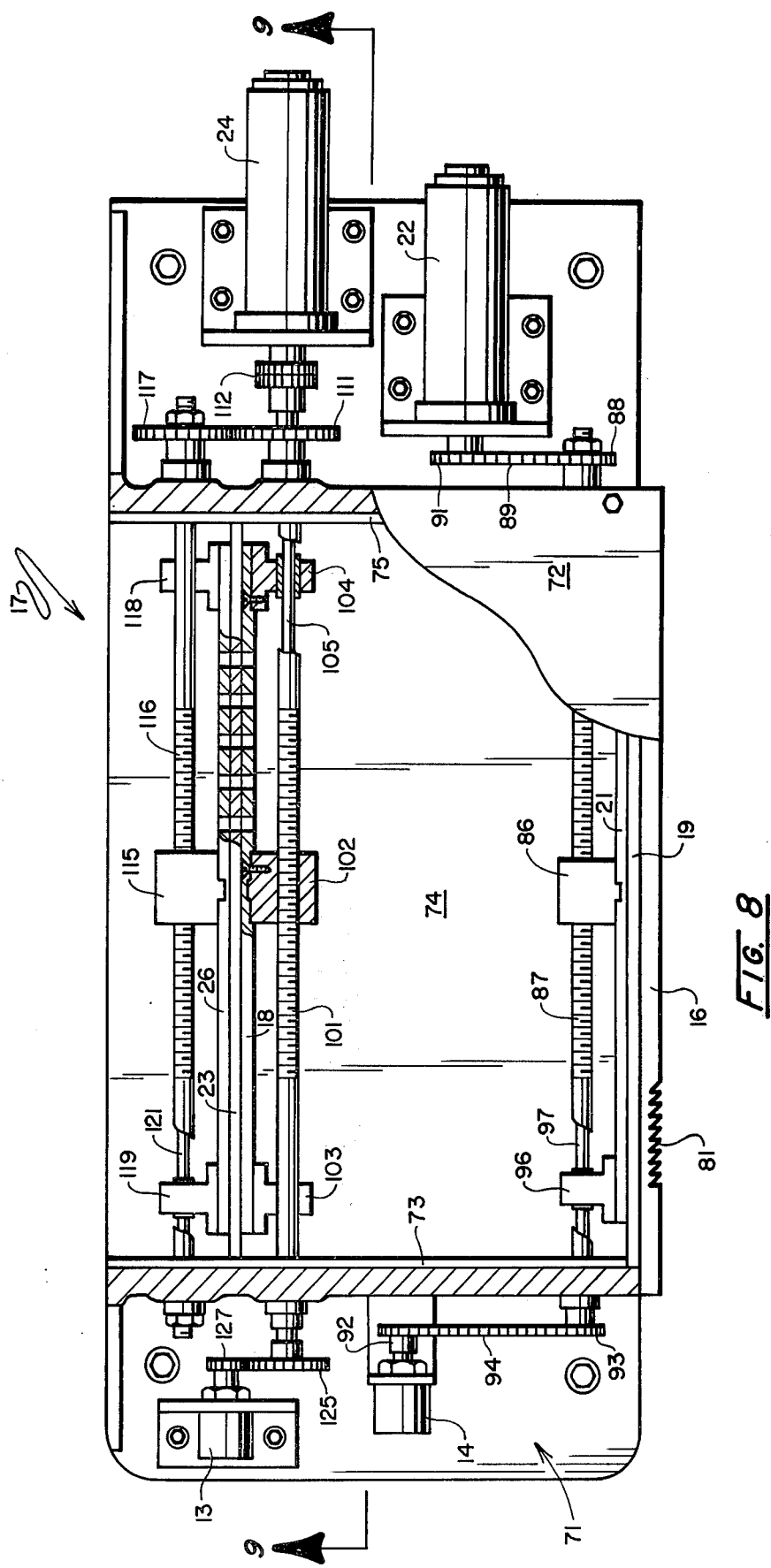
FIG. 8 is a top view of the receiver collimator with portions thereof broken away and shown in section to more fully illustrate the details of the construction thereof.

Referring now to FIG. 8, there is shown a plan view of the receiver collimator 17 with parts thereof broken away and shown in section. The receiver collimator 17 is comprised generally of housing 71 which, in the exemplary embodiment, is an aluminum casting. The housing 71 in cooperation with cover plate 72 defines a collimator space in which are disposed the fixed and movable aperture plates described below. Also situated in this collimator space are a series of interlocking lead shield plates designated 73 through 76. The interlocking shield plates 73 through 76 are designed to confine the travel of X-ray beams through the receiver collimator to a predetermined path.

Figure 11:
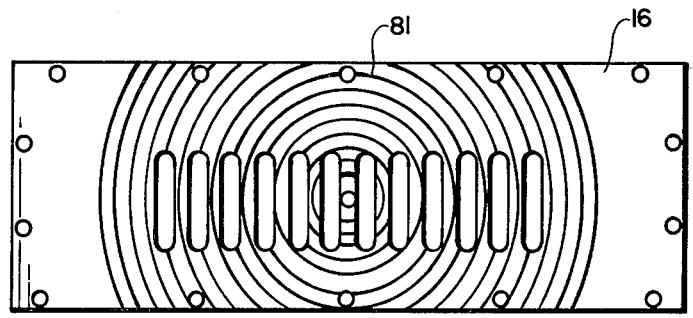

To the front or source end of the housing 71 is affixed lead scatter plate 16 which has a series of 12 rectangular openings therein. These openings, as more fully illustrated in FIG. 11, are slightly larger than the theoretical beam size at this point and are not intended to influence beam size or shape. The face of the scatter plate 16 has machined into it a series of concentric grooves 81 forming generally a saw-toothed cross-section. These grooves extend in all directions from the center of the plate 16 to a distance far enough to encompass the maximum area of possible X-ray penumbra released from the source collimator through the patient compartment. The grooves 81 are intended to create labyrinth effect for the purpose of absorbing uncollimated X-rays.

Figure 12:
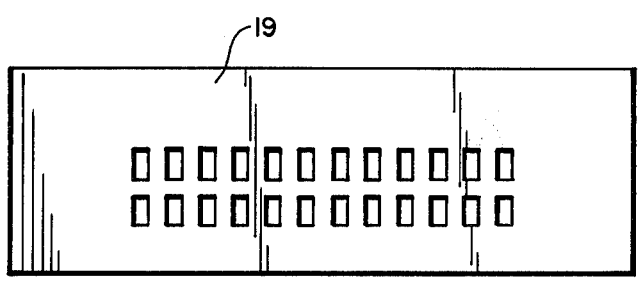

Disposed within receiver collimator housing 71 adjacent to scatter plate 16 is a fixed aperture plate 19 whose details of construction are shown more fully in FIG. 12. The fixed aperture plate 19 has a series of 24 rectangular openings through it arranged in two separate rows of 12 openings each. The fixed aperture plate 19 serves two purposes. First, it divides what is at this point 12 long, narrow rectangular beams into 24 separate rectangular beams, thereby creating two separate slices of information which are contiguous at the center line of the scan circle. Second, the fixed aperture 19 also determines beam thickness.

Figure 13:
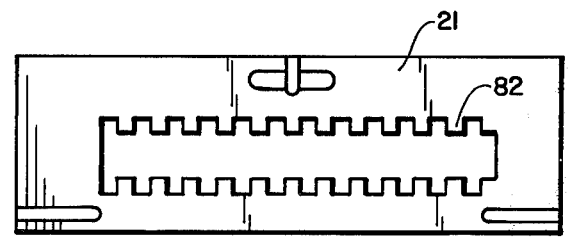

Adjacent to the fixed aperture plate 19 and disposed within the collimator space is a movable aperture 21 whose configuration is more fully disclosed in FIG. 13. The movable aperture plate 21 is adapted to be laterally displaced relative to the fixed aperture plate by means described below in more detail. The movable aperture plate 21 contains a series of 12 rectangular openings in the same relative location as those openings in the aperture plate 19. The openings in the movable aperture plate 21, however, are slightly larger than those openings in the fixed aperture plate 19 in order to not affect the beam size. In addition, the movable aperture plate 21 has a series of 12 smaller openings situated between the larger rectangular openings and contiguous therewith. The placement of these smaller openings between the larger openings creates a saw-toothed type aperture as shown in FIG. 13.

When the movable aperture plate 21 is displaced along its length relative to the fixed aperture plate 19 by means described in more detail below, the protrusions 82 of the movable aperture plate 21 will cover the upper and lower portions respectively of the upper and lower rows of openings in the fixed aperture plate 19, thereby effecting smaller openings than existed when the large rectangular openings of the movable aperture plate 21 were in alignment with the openings of fixed aperture plate 19. The smaller openings resulting from the fixed aperture plate 19 co-acting with the movable aperture plate 21 produce a reduced beam width. It should be noted that the movable aperture plate 21 does not alter the location of the inner edge of the X-ray beams, i.e., the edge nearest to the central line and, therefore, does not affect the contiguousness of two slices of X-ray beams.

The movable aperture plate 21 is particularly adapted to being displaced along its length in a manner similar to that used to displace movable aperture plates 18 and 26.

Affixed to the upper portion of the movable aperture plate 21 is a screw thread follower 86. The screw thread follower 86 engages the threads of the lead screw 87. The lead screw 87 runs parallel to the movable aperture plate 21 and into bearing assemblies in the receiver collimator 71 near each end. An one end of the lead screw 87 there is affixed a sprocket 88 in engagement with a chain 89 which is in further engagement with a sprocket 91 fixedly attached to the output shaft of motor 22. In the exemplary embodiment, the motor 22 is preferably an electric gear motor.

At the opposite end of the lead screw 87 there is fixedly attached a sprocket 93 in engagement with a chain 94 which further engages sprocket 92 fixedly attached to the output shaft of a potentiometer 14. The potentiometer 14 is utilized to provide a shaft position feedback to the control circuitry of the motor 22 as described in more detail below. Attached to the lower portion of movable aperture plate 21 are two linear bearng blocks 96 which ride on a shaft 97 which is affixed to each side of the collimator housing 71.

There is thus provided a means for displacing the movable aperture plate 21 along its length by electrically actuating the motor 22 to cause the lead screw shaft 87 to rotate, which in turn causes the movable aperture plate to be displaced via the screw thread follower 86. The potentiometer provides an electrical feedback to the control circuitry indicative of the position of the movable aperture plate 21. When the operator elects to use either an 8 millimeter or 13 millimeter slice thickness, the select switch is indexed to the appropriate setting. This action permits the output of the potentiometer 14 to cause the motor 22 to start, rotate clockwise or counterclockwise and stop at a predetermined position. The motor 22 thus turns the lead screw thereby moving the screw thread follower 86 and the attached movable aperture plate 21 to either a masked or an unmasked position as more fully described below. It should be noted that neither the fixed aperture plate 19 nor the movable aperture plate 21 affect in any way the width of the X-ray beam.

Figure 15:
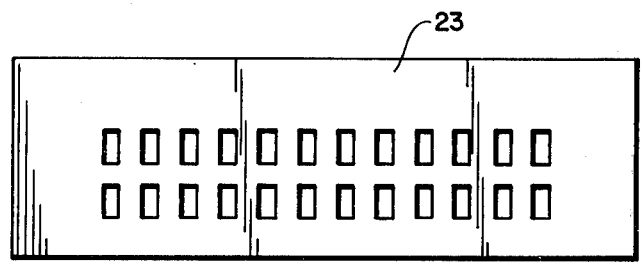

Near the exit end of the collimator 17 are three aperture plates designated 18, 23, and 26. The center aperture plate 23 is a fixed aperture plate having a series of 24 rectangular openings therein as more fully illustrated in FIG. 15. The openings in the fixed aperture plate 23 are arranged in two rows of 12 openings similar to the arrangement of fixed aperture plate 19. The openings in the fixed aperture plate 23 are greater on all sides than the actual beam size and function only to prevent X-rays from passing around the two movable aperture plates 18 and 26 adjacent to it, which plates are smaller than the opening in the collimator space in the housing 71.

The movable aperture plates 18 and 26 have a means similar to that of movable aperture plate 21 for causing the displacement thereof. In particular, associated with movable aperture plate 18 is lead screw 101, and screw thread follower 102. Along the lower portion of the movable aperture plate 18 are linear bearing blocks 103 and 104 which ride on fixed shaft 105. The lead screw 101 rides in bearings affixed in each side of the housing 71 and extends therethrough. Attached to one end of the shaft is a gear 111 and a chain coupling 112, which coupling mechanically couples the lead screw 101 with the output shaft of gear motor 24. Similarly attached to movable aperture 26 is a screw thread follower 115 which engages lead screw 116 which is similarly disposed in each side of the housing. Affixed to one end of the lead screw 116 is a gear 117 which is in engagement with gear 111. The bearing blocks 118 and 119 are affixed to the lower part of the movable aperture plate 26 and move along shaft 121 which has its ends attached to the housing 71. It should also be noted there is affixed to the opposite end of the lead screw 101 a gear 125 which is in engagement with gear 127 which is fixedly attached to the output shaft of the potentiometer 13.

Figure 16:
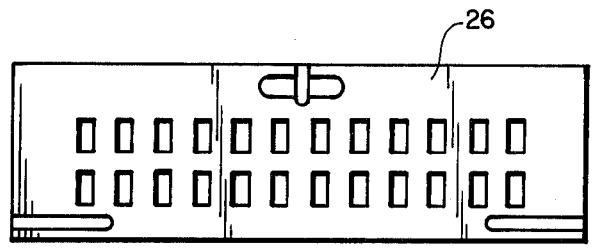
FIGS. 11 through 16 are front elevations of the various aperture plates associated with the receiver collimator.
Figure 14:
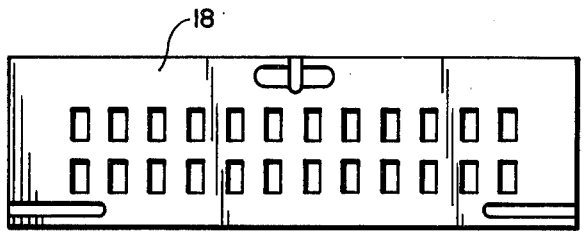

It may now be appreciated that when the motor 24 is electrically actuated, the lead screw 101 is driven via the coupling 112 in one direction while the lead screw 116 will be driven via gears 111 and 117 in the opposite direction. The effect of this motion will cause the openings in the two movable apertures 18 and 26 to move either into or out of alignment thus creating a larger or smaller aperture opening for the X-ray beams to pass through to thereby change the beam width. This action may be more fully appreciated by referring to FIGS. 14 through 16 which illustrate the aperture plates 18 and 26. It may be noted that opposite relative displacement of the movable aperture plates 18 and 26 along their length will cause the edges of the movable aperture plates to be displaced to thereby cause an increase or a decrease in the effective aperture opening of the group of plates comprising variable aperture plate 18, and movable aperture plate 26. It should be noted that the equal relative displacement of plates 18 and 26 causes a variation in beam width without changing the relative position of the center line of each beam.

The potentiometer 13 provides an electrical feedback to the control circuitry as described below of the position of the movable aperture plates. The desired slice width is selected remotely by means of a control switch, and as previously described for the aperture plates 19 and 21, the movable aperture plates 18 and 26 are automatically positioned by control circuitry more fully described below.

Figure 17:
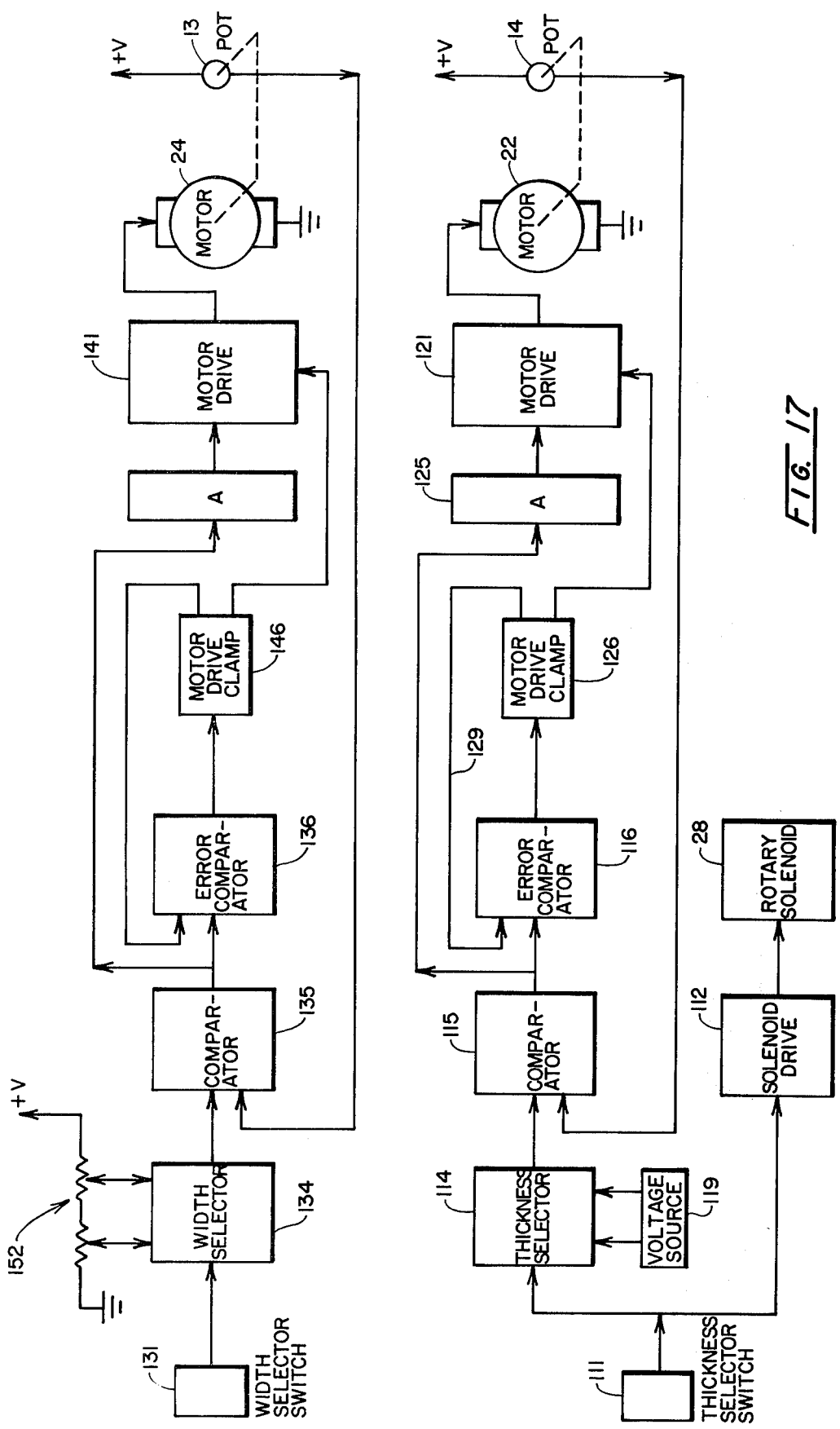
FIG. 17 is a block diagram illustrating the control circuitry of the exemplary embodiment.

Referring now to FIG. 17 of the drawings, there is disclosed the circuitry provided for controlling the movable aperture plates contained within the source and receiver collimators 33 and 17, respectively. The thickness select switch 111 is utilized by the scanner operator to selectively cause the movable aperture plates within the source and receiver collimators to be displaced so that the thickness of the X-ray beams transmitted through the source and receiver collimators may be varied.

In the exemplary embodiment, two beam thicknesses are optionally provided. A first beam thickness is provided during a first state when the movable aperture plate 38 is displaced such that it is not disposed within the beam path and the movable aperture 21 has the openings thereof in alignment with the large openings in the fixed aperture plate 19 so that the shape of the X-ray beams transmitted through the movable aperture plate 21 is substantially determined by the aperture plate 19.

When it is desired to decrease the thickness of the X-ray beams utilized by the scanner, the thickness select switch 111 is actuated to cause the movable aperture plates 38 and 21 to be displaced in a manner such that the movable aperture plates 38 and 21 shape the X-ray beam. Specifically, when the thickness select switch 111 is switched from a first to a second state, a signal corresponding to the second state is transmitted to the solenoid drive circuit 112, which in turn energizes rotary solenoid 28 to cause a displacement of the movable aperture plate 38 to a position adjacent fixed aperture plate 29. This position is more fully disclosed in FIGS. 2 and 3 of the drawings.

In addition, when the thickness select switch 111 is switched to the second state, a signal corresponding thereto is also transmitted to a thickness selector means 114. The thickness selector means 114 may be comprised of an analog multiplexer that selects one of two reference voltages from a voltage source 119 and causes the selected reference voltage to be outputted to a position comparator 115. The position comparator 115 has a second input means for receiving an input from the potentiometer 14. The output of the potentiometer 14 is a voltage level which varies in accordance with the position of the movable aperture plate 21.

The position comparator 115 will compare the selected voltage from the thickness selector means 114 to the voltage output provided by the potentiometer 14 and will generate an error signal when a difference exists between the potentiometer output voltage and the selected reference voltage. A positive output error signal will be provided by the position comparator 115 when the selected reference voltage is smaller than the potentiometer output voltage, and a negative error signal will be provided when the selected reference voltage is larger than the potentiometer output voltage. In the exemplary embodiment, the first reference voltage is +4.5 volts and the second reference voltage is +3.0 volts. The first and second reference voltages are associated with the first and second states, respectively. Because the gain of the position comparator 115 is typically a gain of 10, a large error voltage of plus or minus 12 volts will typically be provided at the output of the position comparator 115 when a change in the switch setting has been made.

The error signal goes from the position comparator 115 to bi-directional motor drive circuit 121 via amplifier 125 and to error comparator 116. Normally, an input to the motor drive 121 causes the motor 123 to rotate and thus causes the movable aperture plate 21 to be displaced as disclosed above. However, a motor drive clamp circuit 126 is provided which is used to selectively disable the motor drive 121.

The motor drive clamp circuit 126 is controlled by the output from error comparator 116. The error comparator 116 is responsive to both positive and negative error signals. The output of the error comparator 116 will toggle between plus and minus 12 volts depending on the level of its input signals. When the thickness select switch 11 is at a preset position, the output of the error comparator 116 is minus 12 volts because the motor drive clamp output feedback 129 maintains a minus 1 volt signal at the non-inverting input of the error comparator 116, and the error signal provided by position comparator 115 is near zero volts. The error signal from comparator 115 must therefore exceed a magnitude plus or minus 1 volt in order to toggle the error comparator 116. This condition occurs only when a new reference voltage corresponding to a new beam is selected by the thickness select switch 111.

When a new beam thickness is selected, an error signal of approximately 12 volts will be outputted by the position comparator 115 to cause the error comparator 116 output to switch to plus 12 volts which will drive the motor drive clamp 126 output to minus 12 volts. The minus 12 volt output of the motor drive clamp 126 produces two results. First, motor clamping is removed from the motor drive; and second, the minus one volt from the motor drive clamp 126 is changed to 0.1V to the error comparator 116 input. This condition allows the movable aperture 21 to gradually approach the desired position where motor clamping is reapplied.

With motor clamping removed, the motor drive circuitry is free to respond to error signals generated by the position comparator 115. The motor drive circuitry includes an error amplifier and a bi-directional motor drive which applies positive or negative voltages to the motor 22.

As the movable aperture 21 is driven into the proper position by the motor 22, the error signal voltage from the position comparator 115 will gradually reduce. When the error signal voltage falls below 800 millivolts, the motor drive circuitry will begin to reduce motor speed to prevent overshooting the desired position. The error signal will continue to decrease until about 100 millivolts. The error comparator 116 will then remove the plus 12 volts to the motor drive clamp 126 which will cause the output of the motor drive clamp 126 to inhibit the motor drive 121 and also change signal 129 from 0.1V back to 1.0V thus increasing the magnitude of the error necessary to turn the circuit back on to ±1.0V. With the movable aperture thus locked in position by the motor clamp circuitry 126, a new image thickness selection is required before the motor 22 will again move.

Similar control circuitry is provided for the drive motor 24 which causes the relative displacement of movable aperture plates 18 and 26. As can be seen from FIG. 17, there is provided a width selector switch 131 which provides an electrical signal to the width select means 134 in accordance with the particular width selected. The width select means 134 is, in the exemplary embodiment, an analog multiplexer similar to that described above which selects one of two reference voltages from a voltage supply and provides one of the reference voltages to a position comparator 135 which also receives an input from potentiometer 13 in a manner similar to the control circuitry described above.

Reference voltage supply 152 consists of two potentiometers, one for each position. Adjustment of these potentiometers provides independent infinitely variable adjustment of the two reference voltages. The availability of infinitely variable inputs to the width select means 134 allows the movable aperture plates displaced by the motor 24 to provide infinitely variable beam widths.

It can not be readily appreciated that the error comparator 135, motor drive clamp 146, motor drive 141, and motor 24 function in a manner analogous to the corresponding elements of the control circuit described above to provide a means for preselecting one of a plurality of beam width selections, which may be infinitely variable, to automatically cause the movable aperture plates 18 and 26 to be displaced relative to each other in order to vary the shape of the X-ray beam transmitted through aperture plates 18, 23 and 26 in the manner described above.

It should be appreciated that the exemplary embodiment described herein utilizes a source collimator having movable aperture means which provide only two beam shapes. It should be realized, however, that the source collimator may have a plurality of movable apertures to afford a greater degree to control of beams of the X-ray transmitted through the source collimator. It should be further appreciated that while the movable aperture plates of the instant invention are intended to be displaced to a limited number of set displacements, the modifications necessary to allow the movable apertures to be displaced in an infinitely variable manner would be obvious to one skilled in the art.

The following claims are intended to cover all modifications which do not depart from the spirit and scope of the invention. The invention is not to be necessarily limited to the specific construction illustrated and described, since such construction is intended to be illustrative of the principle of operation and the means presently devised to carry out said principle. It is to be considered that the invention comprehends any minor change in construction that is permitted within the scope of disclosure.

The invention claimed is:

1. In a computerized axial tomographic scanner having a source of radiation, a subject receiving area, radiation detection means, a first collimator means having radiation from said source of radiation passing therethrough, and a second collimator means having radiation from said source of radiation passing therethrough, the improvement comprising:

a first variable aperture means associated with said first collimator means for varying the radiation passing therethrough;
a second variable aperture means associated with said second collimator means for varying the radiation passing therethrough; and
control means for causing said second variable aperture means of said second collimator means to coact with said first variable aperture means of said first collimator means.

2. The apparatus as set forth in claim 1 wherein said control means causes said first variable aperture means to vary at least one dimension of at least one aperture and causes said second variable aperture means to vary by a corresponding amount at least one dimension of at least one aperture.

3. In computerized tomographic scanner, a variable collimator means, comprising:
   (a) a source of radiation emitting a beam;
   (b) a subject receiving area having said beam passing therethrough;
   (c) a first collimator means disposed between said source of radiation and said subject receiving area wherein said first collimator means has first variable aperture means;
   (d) radiation detection means in substantial axial alignment with said beam of radiation;
   (e) a second collimator means disposed between said subject receiving area and said radiation detection means, wherein said second collimator has second variable aperture means for varying the amount of radiation received by said radiation detection means from said source of radiation; and
   (f) wherein said first variable aperture means of said first collimator means cooperatively interacts with said second variable aperture means of said second collimator means such that varying the aperture of one of said collimator means produces a corresponding variation of the aperture of the other of said collimator means.

4. The apparatus as set forth in claim 3 wherein said first collimator means includes a first linear array of apertures for dividing said beam of said source of radiation into a plurality of beams.

5. The apparatus as set forth in claim 4 wherein said second collimator means includes a second linear array of apertures, one corresponding to each aperture of said first linear array.

6. The apparatus as set forth in claim 5 wherein said first and second variable aperture means vary at least one dimension of each aperture of said first and second linear arrays of apertures, respectively.

7. The apparatus as set forth in claim 6 wherein said first and second variable aperture means vary each aperture of said first and second linear array correspondingly in dimensions generally transverse to said linear arrays.

8. The apparatus as set forth in claim 6 wherein said first and second variable aperture means discretely vary at least one dimension of each aperture of said first and second linear arrays between preselected aperture dimensions.

9. The apparatus as set forth in claim 6 further including control means operatively connected to said first and second variable aperture means for varying at least one dimension of each aperture of said first and second linear arrays, and selector means operatively connected with said control means for selecting said at least one dimension whereby at least one dimension of the radiation beams can be remotely varied.

10. Control means for a first variable collimator having a first movable aperture means and a second coacting variable collimator having a second movable aperture means comprising:
   (a) first drive means for displacing said first movable aperture means;
   (b) position responsive means having an output indicative of the position of said first movable aperture means;
   (c) an aperture selection means having an output indicative of a selected corresponding aperture for said first and second variable collimators;
   (d) comparator means receiving the output of said position responsive means indicative of the position of said first movable aperture means and the output of said aperture selection means indicative of a selected aperture;
   (e) drive control means responsive to the output of said comparator means for causing said drive means to displace said first movable aperture means and
   (f) second drive means operatively connected with said aperture selection means for displacing said second movable aperture means.

11. In an apparatus for measuring the attenuation of radiation after passage through a medium and for reconstructing a representation of the medium, the apparatus including a source of radiation mounted to pass radiation through the medium, a radiation detection means on the side of the medium opposite the source, means for causing a relative movement of at least the source of radiation with respect to the medium in order that the radiation passes through the medium along a plurality of paths along each of which radiation is attenuated and the attenuated radiation detected by the detection means, the improvement comprising:
   a variable aperture means disposed between said source and said detection means comprising:
   a fixed shaping means having at least a first aperture therein for shaping radiation passing therethrough into at least one beam, said first aperture having plurality of dimensions for shaping the cross-sectional dimensions of the beam;
   a movable shaping means having at least a second aperture therein mounted for displacement relative to said fixed shaping means, said second aperture having at least one dimension smaller than said first aperture, whereby the second aperture is movable to reduce at least one cross-sectional dimension of the beam; and
   control means operatively connected with said movable shaping means for moving said movable shaping means at least between a first position in which said second aperture is displaced from said first aperture such that the radiation passes through said first aperture to the exclusion of said second aperture, whereby the first aperture shapes the cross section of the beam, and a second position in which said second aperture is disposed adjacent said first aperture such that the radiation passes through said first and second aperture whereby the first and second apertures cooperate to shape the cross-sectional dimensions of the beam.

12. The apparatus as set forth in claim 11 wherein said fixed shaping means has a plurality of generally rectangular apertures for shaping a plurality of beams having generally rectangular cross sections defined by width and thickness dimensions.

13. The apparatus as set forth in claim 11 wherein said movable shaping means is pivotally mounted whereby said control means rotates said movable shaping means between the first and second positions.

14. The apparatus as set forth in claim 11 further including a second variable aperture means disposed between said source and said detection means for variably shaping the cross-sectional dimensions of the beam, said control means operatively connected with said second variable aperture means.

15. In an apparatus for measuring the attenuation of radiation after passage through a medium and for reconstructing a representation of the medium, the apparatus including a source of radiation mounted to pass radiation through the medium, a detector means for the radiation on the side of the medium opposite the source, means for causing a relative movement of at least the source of radiation with respect to the medium in order that the radiation passes through the medium along a plurality of paths along which radiation is attenuated and detected by the detector means, the improvement comprising:
   a fixed shaping means having at least a first aperture therein, and so positioned that radiation from the source passes through said first aperture, said first aperture having a plurality of dimensions for shaping the radiation passing therethrough into a beam having corresponding cross-sectional dimensions;
   a first movable shaping means having at least a second aperture therein and so movably positioned adjacent said fixed shaping means that said first and second apertures are at least partially aligned; and
   displacing means operatively connected with said first movable shaping means for displacing said first movable shaping means relative to said fixed shaping means to change the alignment of said first and second apertures, whereby at least one cross-sectional dimension of the beam is changed.

16. The apparatus as set forth in claim 15 wherein said fixed shaping means further includes a plurality of grooves generally saw-toothed in cross section disposed toward said source for absorbing uncollimated radiation.

17. The apparatus as set forth in claim 15 wherein said movable shaping means is displaceable between at least a first and a second position, and wherein said second aperture includes at least one projection so positioned that in said first position said projection is out of alignment with said first aperture, and in said second position said projection is in alignment with said first aperture whereby the cross section of the beam is reduced in at least one dimension as the movable shaping means is displaced from said first position to said second position.

18. The apparatus as set forth in claim 17 wherein said fixed shaping means has a plurality of apertures for shaping a plurality of beams, and wherein said second aperture has a plurality of projections, one corresponding to each of the plurality of apertures and so positioned that in said first position one of said projections is in alignment with each of said plurality of apertures, and in said second position each of said projections is out of alignment with any said plurality of apertures whereby the cross section of the plurality of beams is reduced in at least one dimension as the movable shaping means is displaced.

19. The apparatus as set forth in claim 18 wherein said plurality of apertures in said fixed shaping means is arranged in at least two substantially parallel linear arrays.

20. The apparatus as set forth in claim 15 further including a second movable shaping means having at least a third aperture therein and so movably positioned adjacent said fixed shaping means and said first movable shaping means that said first, second and third apertures are at least partially aligned, said displacement means operatively connected with said second movable shaping means for displacing said second movable shaping means relative to at least said fixed shaping means.

21. The apparatus as set forth in claim 20 wherein said displacing means displaces said first and second movable shaping means relative to said fixed shaping means in opposite directions and by equal spatial amounts.

22. The apparatus as set forth in claim 20 wherein said fixed shaping means includes a first linear array of apertures, said first movably shaping means includes a second substantially linear array of apertures disposed substantially parallel with said first linear array, said second movable shaping means includes a third substantially linear array of apertures disposed generally parallel to said first and second linear arrays, said first, second and third linear arrays disposed in generally overlapping position, and wherein said displacing means slides the second and third arrays relative to the first array to vary the degree of overlap whereby each beam is shaped by apertures in said first, second and third arrays.

23. The apparatus as set forth in claim 20 wherein said displacing means includes a screw thread means, a first screw thread follower operatively connected to said first movable shaping means engaging said screw thread means, a second screw thread follower operatively connected to said second movable shaping means engaging said screw thread means, and means for rotating said screw thread means whereby the first and second screw thread followers are moved along the screw thread means to move the first and second movable shaping means.

24. The apparatus as set forth in claim 23 wherein said screw thread means includes first and second screw threads engaging said first and second screw thread followers respectively, said first and second screw threads so pitched and rotated that said first and second screw thread followers move equal distances in opposite directions as the first and second screw threads rotate.

25. In an apparatus for measuring the attenuation of radiation after passage through a medium and for reconstructing a representation of the medium, the apparatus including a source of radiation mounted to pass radiation through the medium, a detector means for the radiation on the side of the medium opposite the source, means for causing relative movement of at least the source of radiation with respect to the medium to give an output fixed shaping means having at least one substantially linear array of apertures and so positioned that radiation from the source passes through the apertures and is shaped into a corresponding array of beams, each having a first dimension parallel to the linear array and a centerline transverse to the linear array and positioned centrally to said first dimension the improvement comprising:
 a variable aperture means for simultaneously adjusting said first dimension of each of said apertures symmetrically about said centerline.

26. The apparatus as set forth in claim 25 wherein the variable aperture means includes a first movable plate having at least one linear array of apertures corresponding to the linear array of the fixed shaping means, a second movable plate having at least one linear array of apertures corresponding to the linear array of the fixed shaping means and displacing means for displacing said first and second plates generally equal distances relative to said centerline in opposing directions.

* * * * *